United States Patent [19]

Holmes

[11] Patent Number: 5,246,848
[45] Date of Patent: Sep. 21, 1993

[54] PROCESS FOR PROVIDING ENHANCED YIELD AND SIMPLIFIED ISOLATION OF HYDROPHOBIC ENZYMES FROM CULTURE MEDIA

[75] Inventor: Paul E. Holmes, Hamden, Conn.

[73] Assignee: Olin Corporation, Cheshire, Conn.

[21] Appl. No.: 703,317

[22] Filed: May 20, 1991

[51] Int. Cl.$^5$ .......................... C12N 9/20; C12N 1/20; C12N 1/00
[52] U.S. Cl. .................. 435/198; 435/253.3; 435/874
[58] Field of Search ...................... 435/198, 183, 253.3, 435/874

[56] References Cited

U.S. PATENT DOCUMENTS

| | | | |
|---|---|---|---|
| 4,179,334 | 12/1979 | Esders et al. | 435/134 |
| 4,665,029 | 5/1987 | Iwai et al. | 435/198 |
| 4,933,287 | 6/1990 | Favin et al. | 435/198 |
| 5,063,160 | 11/1991 | Holmes | 435/198 |

FOREIGN PATENT DOCUMENTS 63-240791 10/1988 Japan.
WO9010695 9/1990 PCT Int'l Appl.

OTHER PUBLICATIONS

Philippe Burgisser, Jean-Marie Matthieu, *Phase Separation of Myelin Proteins in Triton X-114*, 1989, 11:179–187.

*Journal of Applied Biochemistry* 7, 356–369 (1985) "Isolation of Human ... Chromatography".
*The Journal of Biological Chemistry*, vol. 256 No. 4, Issue of Feb. 25, pp. 1604–1607, 1981, vol. 259, No. 23, Issue of Dec. 10, pp. 14922–14927, 1984, vol. 233, pp. 525–533, 1986 (Printed in Great Britain).
*Analytical Biochemistry* vol. 153, pp. 330–335 (1986)—"Phase Separation of Rat Intestinal Brush Border Membrane Proteins Using Triton X–114".

Primary Examiner—David M. Naff
Assistant Examiner—Michael V. Meller
Attorney, Agent, or Firm—Dale Lynn Carlson

[57] ABSTRACT

This invention is directed to a process for providing enhanced yield and simplified isolation of hydrophobic enzymes from a culture medium. The process comprises the steps of: (a) culturing a hydrophobic enzyme-secreting microorganism in an aqueous culture medium comprising a yield-enhancing effective amount of a nonionic surfactant having a cloud point of less than 40° C. for a time sufficient to provide enhanced secretion of said enzyme from said microorganism, (b) removing said microorganism from said culture medium to provide a microorganism-free solution, (c) heating said microorganism-free solution to a temperature above said cloud point to cause phase separation of said culture medium into an aqueous phase, and a non-aqueous phase containing said nonionic surfactant and said yield-enhanced hydrophobic enzyme, and (d) isolating said non-aqueous phase containing said nonionic surfactant and said yield-enhanced hydrophobic enzyme.

3 Claims, No Drawings

PROCESS FOR PROVIDING ENHANCED YIELD AND SIMPLIFIED ISOLATION OF HYDROPHOBIC ENZYMES FROM CULTURE MEDIA

FIELD OF THE INVENTION

This invention relates generally to a new process for providing yield enhancement and fascile isolation of hydrophobic enzymes from a culture medium. The invention is particularly suitable for providing improved yield and separation of lipase enzymes from a culture medium containing the enzyme.

BACKGROUND OF THE INVENTION

Recently, lipases have become of interest as laundry detergent additives. By way of illustration, Novo Industri A/S has recently introduced into the marketplace a lipase referred to as LIPOLASE. However, the present inventor has found that LIPOLASE is not as effective as might be desired in performing its function of breaking down lipids into fatty acids, and the LIPOLASE stability is less than might be desired in laundry detergent formulations. Thus, other lipase compositions exhibiting enhanced cleaning efficacy and/or lipase stability are highly desired by the detergent manufacturing community.

The present inventors have previously isolated a biologically pure culture of a previously undescribed strain of *Pseudomonas alcaligenes,* strain SD2, ATCC 53877 as disclosed and claimed in co-pending, commonly-assigned U.S. application Ser. No. 07/324,062 now U.S. Pat. No. 5,063,160, issued Nov. 5, 1991, incorporated herein by reference in its entirety, and published on Sep. 20, 1990 as International Publication No. WO 90/10695. The organism is a natural isolate and has been deposited on Mar. 2, 1989 with the American Type Culture Collection at Rockville, Md. (ATCC), having been assigned the accession number ATCC 53877. This novel strain SD2 was found to produce a novel lipase. However, heretofore the yields of the lipase, and its ease of separation from the culture medium, have been less than might be desired.

New processes for providing enhanced yield and simplified isolation of lipase and other hydrophobic enzymes produced by microorganisms, such as *Pseudomonas alcaligenes* strain SD2, from a culture medium would be highly desired by the detergent manufacturing industry. Heretofore, such methodology has not been known to the knowledge of the present inventor.

SUMMARY OF THE INVENTION

In one aspect, the present invention relates to a process for providing enhanced yield and simplified isolation of hydrophobic enzymes from a culture medium which comprises the steps of:

(a) culturing a hydrophobic enzyme-secreting microorganism in an aqueous culture medium comprising a yield-enhancing effective amount of a nonionic surfactant having a cloud point of less than 40° C. for a time sufficient to provide enhanced secretion of said enzyme from said microorganism, (b) removing said microorganism from said culture medium (preferably at a temperature below said cloud point) to provide a microorganism-free solution, (c) heating said microorganism-free solution to a temperature above said cloud point to cause phase separation of said culture medium into an aqueous phase, and a non-aqueous phase containing said nonionic surfactant and said yield-enhanced hydrophobic enzyme, and (d) isolating said non-aqueous phase containing said nonionic surfactant and said yield-enhanced hydrophobic enzyme.

In another aspect of the present invention, steps (b) and (c) of the above-process are carried out simultaneously.

In yet another aspect, the present invention relates to a process for providing enhanced yield and simplified isolation of a lipase produced by the microorganism *Pseudomonas alcaligenes* strain SD2 from a culture medium which comprises the steps of:

(a) culturing the microorganism *Pseudomonas alcaligenes* strain SD2 in an aqueous culture medium comprising a yield-enhancing effective amount of polyoxyethylene p-t-octylphenol having a cloud point of less than 40° C. for a time sufficient to provide enhanced secretion of said lipase from said microorganism *Pseudomonas alcaligenes* strain SD2, (b) removing said microorganism *Pseudomonas alcaligenes* strain SD2 from said culture medium (preferably at a temperature below said cloud point) to provide a microorganism-free solution, (c) heating said microorganism-free solution to a temperature above said cloud point to cause phase separation of said culture medium into an aqueous phase, and a non-aqueous phase containing said polyoxyethylene p-t-octylphenol and said yield-enhanced lipase, and (d) isolating said non-aqueous phase containing said polyoxyethylene p-t-octylphenol and said yield-enhanced lipase.

These and other aspects will become apparent upon reading the following detailed description of the invention.

DETAILED DESCRIPTION OF THE INVENTION

The nonionic surfactants useful in the present invention have a cloud point of less than 40° C., such as, for example, octylphenoxypolyethoxy ethanol (commercially available as TRITON® X-114, a product of Rohm & Haas Company), oxyethylated alcohols (commercially available as PLURAFAC® RA40, a product of BASF Corporation), polyethoxylated alcohols (commercially available as TRITON® DF-12, a product of Rohm & Haas Company), aliphatic polyethers (commercially available as ANATROX® BL-330, a product of GAF Corporation), EO/PO alkoxylated secondary alcohols (commercially available as TERGITOL® Minfoam 2X, a product of Union Carbide Corporation) and polyoxyethylene oleyl ether (commercially available as BIRJ® 96, a product of ICI Americas, Inc.), and combinations thereof. The nonionic surfactant is employed in a "yield enhancing amount", i.e., an amount sufficient to enhance the yield of the desired hydrophobic enzyme. The weight/volume concentration of the nonionic surfactant employed in the process of the present invention is preferably between about 0.5 and about 10%, more preferably between about 0.5 and about 1% by weight based upon the volume of the culture medium.

Hydrophobic enzymes useful in the process of the present invention are preferably lipase enzymes, such as those produced by fungi or bacteria. Illustrative microorganism are those having a genus selected from the group consisting of Aspergillus, Geotrichum, Humicola, Penicillium, Rhizopus, Streptococcus, Pseudomonas, Chromobacterium, Pseudomonas and Bacillus. Thus, typical lipase-producing fungi include *Aspergillus niger, Geotrichum candidum, Humicola lanuginosa, Penicillium cyclepium,* and *Rhizopus delemar.* Typical lipase-producing bacteria include *Streptococcus faecalis, Pseudomonas nitroreducens, Chromobacterium viscosum, Pseudomonas fluorescens,* and *Bacillus subtilis.* Preferred lipases are those produced by *Pseudomonas alcaligenes* and *Pseudomonas pseudoalicaligenes,* most preferably *Pseudomonas alcaligenes,* strain SD2.

The microorganism, *P. alcaligenes,* strain SD2, was isolated from a shower drain by direct isolation on a Tryptone-Soytone-Olive oil isolation medium, as described more fully in copending U.S. application Ser. No. 07/324,062, incorporated herein by reference in its entirety. The isolation medium employed is more fully described in Table I below.

TABLE I

| Isolation Medium | |
|---|---|
| | Percent by Weight |
| Ammonium sulfate | 0.5 |
| Potassium phosphate, dibasic | 0.05 |
| Magnesium sulfate, heptahydrate | 0.025 |
| Tryptone (Difco) | 1.7 |
| Soytone (Difco) | 0.3 |
| Olive oil | 1.0 |
| Rhodamine B | 0.001 |
| Agar | 1.5 |

The Rhodamine B dye in the isolation medium causes lipase-producing bacterial colonies to fluoresce an orange color when irradiated with long wavelength ultraviolet light (Kouker, G. and K.-E. Jaeger, 1987, *Appl. Environ. Microbiol.,* 53: 211-3). This fluorescence permits the easy identification of lipase-producers. Colonies so identified were purified by restreaking onto similar media. Stock cultures were maintained on Difco TSA slants.

The bacterial isolate was identified using standard taxonomic procedures from *Bergey's Manual of Systematic Bacteriology* (Williams & Wilkins, Baltimore, 1984). The results of applicable physiological characterization tests of *P. alcaligenes* strain SD2 are presented in Table II and compared with characteristics of *P. alcaligenes* and *P. pseudoalicaligenes* published in Bergey's Manual.

TABLE II

Substrate Utilization of *P. alcaligenes* Strain SD2, *P. alcaligenes,* and *P. pseudoalicaligenes*

| | Strain* | | |
|---|---|---|---|
| | SD2 | P. alcaligenes | P. pseudoalicaligenes |
| Fructose | − | − | + |
| L-aspartate | + | − | − |
| L-glutamate | − | + | + |
| D-gluconate | − | − | d |
| L-Histidine | − | d | d |
| Ethanolamine | − | − | + |
| n-Butanol | − | d | + |
| Isobutanol | + | d | − |
| Citrate | − | d | d |
| Betaine | − | − | + |
| Glycerol | − | − | d |
| Sorbitol | − | − | d |

TABLE II-continued

Substrate Utilization of *P. alcaligenes* Strain SD2, *P. alcaligenes,* and *P. pseudoalicaligenes*

| | Strain* | | |
|---|---|---|---|
| | SD2 | P. alcaligenes | P. pseudoalicaligenes |
| Itaconate | − | − | d |

Abbreviation:
d (11-80 percent of strains positive);
+ (strain was able to utilize the indicated chemical for growth);
− (strain did not utilize the chemical for growth).
*Data for *P. alcaligenes* and *P. pseudoalicaligenes* are from Bergey's Manual of Systematic Bacteriology (Williams & Wilkins [Baltimore, 1984]).
Compounds utilized by all strains include:
DL-lactate, succinate, fumarate, acetate, L-arginine, caprate, and L-malate.
Compounds not utilized by any strain include:
D-glucose, L-arabinose, D-mannose, D-mannitol, L-rhamnose, D(+)-galactose, D(−)-ribose, m-inositol, L-threonine, m-tartrate, adipate, phenylacetate, nicotinate, sebacate, suberate, benzoate, and pimelate.

This table illustrates nutritional capabilities of the indicated strains and further illustrates their differences.

Several lipase-producing strains of *P. pseudoalicaligenes* are disclosed in International Publication No. WO 87/00859 published under the Patent Cooperation Treaty. Table III presents certain morphological and physiological characteristics of *P. alcaligenes* strain SD2, as compared to the characteristics of four strains of *P. pseudoalicaligenes* disclosed in International Publication No. WO 87/00859. Differences between the SD2 strain of the present invention and the other strains are readily apparent. For example, SD2 utilized L-aspartate, while the two other Pseudomonas species did not, as noted noted in Table II.

TABLE III

Characteristics of *P. alcaligenes* Strain SD2 and Selected Lipase-Producing Strains of *P. pseudoalicaligenes.*
(The CBS Strain Accession Numbers Correspond to Those Referenced in International Publication No. WO 87/00859)

| | Comparison Strains | | | | |
|---|---|---|---|---|---|
| Characteristic | Strain of Invention SD2 | CBS 467.85 | CBS 468.85 | CBS 471.85 | CBS 473.85 |
| Cell shape | rod | rod | rod | rod | rod |
| Motility | + | + | + | + | + |
| Spores | − | − | − | − | − |
| Gram strain | − | − | − | − | − |
| Oxidase | + | + | + | + | + |
| Anaerobic glucose | − | − | − | − | − |
| Aerobic glucose | − | − | − | − | − |
| Aerobic maltose | − | − | − | − | − |
| Aerobic sucrose | − | − | − | − | − |
| Aerobic D-xylose | − | − | − | − | + |
| Arginine dihydrolase | + | + | + | − | + |
| Gelatin hydrolysis | − | − | − | − | − |
| Starch hydrolysis | − | − | − | − | − |
| $NO_3^- \rightarrow NO_2^-$ | + | + | + | + | + |
| $NO_2^- \rightarrow N_2$ | + | − | − | − | − |
| Citrate Utilization | − | + | + | + | + |
| Catalase | + | + | + | + | + |
| Growth at 41° C. | + | + | + | + | + |

Strain SD2 of the present invention can be grown in various types of culture media under conditions suitable for growth of pseudomonads. Typically, such media contain assimilable sources of carbon, nitrogen, and various inorganic mineral nutrients. By way of illustration, *P. alcaligenes* strain SD2 was grown in Tryptone Medium having the formulation as shown in Table IV.

TABLE IV

| Ingredient | Culture Medium Percent by Weight |
| --- | --- |
| Ammonium sulfate | 0.5 |
| Potassium phosphate, dibasic | 0.05 |
| Magnesium sulfate, heptahydrate | 0.025 |
| Tryptone (Difco) | 2.0 |
| BRIJ(R) 58 | 1.0 mM |

The lipase of the invention is found in culture media, preferably liquid media, containing P. alcaligenes strain SD2. Quantities of this enzyme can be obtained by culturing P. alcaligenes strain SD2 in liquid culture and under culture conditions suitable for growth of organisms of this type. For example, an actively growing aliquot of P. alcaligenes strain SD2 is suitably used as an innoculum and introduced into Erlenmeyer flasks containing Tryptone medium (C.F. Table IV). Cultures are incubated with shaking for about 24 hours at a temperature of about 30° C. Following this culture growth period, the bacterial cells are removed by centrifugation or filtration or other suitable techniques. The lipase which is found in the resultant clarified culture liquor is then generally concentrated prior to use. Several methods may be used to concentrate this enzyme, including ultrafiltration as discussed in Example 1.

It is desirable that lipases intended for commercial utilization be stable in the presence of various surfactants commonly found in cleaning product formulations. Advantageously, the lipase of P. alcaligenes strain SD2 was found to be functional in the presence of commercial surfactants such as dodecylbenzene sulfonate and fatty alcohol ethoxylates. In addition, the inclusion of the non-ionic surfactant BRIJ ® 58 [polyoxyethylene (20) cetyl ether] in liquid growth medium containing P. alcaligenes strain SD2 at a 1-10 mM concentration, preferably 1 mM, increased the yield of the lipase by a factor of two-fold or more in contrast to control cultures without this surfactant.

Regarding the stability of the lipase produced by P. alcaligenes strain SD2, this enzyme loses activity during storage at a rate that is directly proportional to temperature. For example, during accelerated aging tests conducted at a temperature of 37° C. and a pH of 7.0, the lipase of the invention demonstrated a half-life of about 5 days in the absence of surfactants. The addition of calcium, in the form of $CaCl_2$, stabilized the SD2 lipase and increased its half-life to over 80 days at suitable $CaCl_2$ concentrations. The concentration of $CaCl_2$ required to enhance such enzyme longevity is related to the particular lipase formulation. For example, in simple buffered enzyme solutions lacking surfactants, where the buffer is, for example, 50 mM BES [N, N-bis (2-hydroxyethyl)-2-amino-ethanesulfonic acid] at pH 7.0, the addition of 5 mM $CaCl_2$, preferably 10 mM, is sufficient. The optimum concentration of $CaCl_2$ in the presence of preferred surfactants is about 25 mM or more. In formulations of the lipase of P. alcaligenes strain SD2, various surfactants can be used in view of this lipase's stability in the presence of surfactants as illustrated in Table VI below. Examples of preferred surfactants include the nonionic surfactant BRIJ ® 58 [Polyoxyethylene (20) cetyl ether] and the anionic surfactant SANDOPAN ® DTC gel. Preferred nonionic surfactants are those having a hydrophobic end containing 12-16 carbon units, and a polyoxyethylene chain size of about 20-23 ethylene oxide units. In general, anionic surfactants of the carboxylated type are preferred and are most compatible with the novel lipase of P. alcaligenes strain SD2.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

EXAMPLE 1

Part (A)- Preparation of Lipase From *Pseudomonas alcaligenes* Strain SD2

The microorganism of the invention, P. alcaligenes SD2, was conveniently grown in the culture medium previously presented in Table IV.

A 50 mL starter culture of P. alcaligenes SD2 in a 250 mL Erlenmeyer flask was grown for about 16 hours at a temperature of 30° C. at 175 rpm on a gyratory shaker. This starter culture was then used to inoculate 8 liters of culture medium divided among 4 and 6 L fluted Erlenmeyer flasks such that no individual flask contained more than 25 percent flask capacity as liquid. The culture flasks thus prepared were incubated for 24 hours at a temperature of 30° C. with gyratory shaking at 150 rpm.

Following the culture period, the lipase of the invention was harvested and concentrated by first removing the bacterial cells from the 8 liters of liquid culture by tangential flow filtration using Filtron $10^6$ (NMWC) Omega membrane cassettes. The resultant cell-free filtrate was then concentrated by tangential flow ultrafiltration using Filtron 30,000 (NMWC) Omega membrane cassettes. Thereafter, the concentrate was diafiltered at 3° C. with about 10 volumes of 50 mM BES, pH 7.0, supplemented with 10 mM $CaCl_2$ in order to eliminate all low molecular weight contaminants (those with molecular weights less than 30,000), and to change the lipase solvent to one with buffer and stabilizing $CaCl_2$. The yields of enzyme from three separate batch cultures are presented in Table V.

TABLE V

| Yields of Lipase Produced by Cultures of P. alcaligenes Strain SD2 | | |
| --- | --- | --- |
| Batch No. | Units/mL[1] | Total Units |
| 20 | 39.15 | 10,571 |
| 21 | 34.69 | 7,840 |
| 22 | 37.41 | 6,172 |

[1] One unit is the amount of lipase which produces one microequivalent of fatty acid from olive oil per minute at 37° C. and at pH 10.

Part (B)— (Comparison) Production of the Lipase P. alcaligenes SD2 & Molecular Weight Measurement Quantities of the lipase of P. alcaligenes strain SD2 were obtained by culturing of the organism in the medium of Table IV, removing the bacterial cells by filtration, concentrating the enzyme by ultrafiltration as already described. Lipolytic activity was assayed using the following standard composition: (i) 2.5 mL substrate [10 percent (w/v) olive oil emulsified in 10 percent (w/v) gum arabic]; (ii) 2.0 mL buffer [1.0M CHES (2[N-cyclohexylamino]-ethane sulfonic acid), pH 10.0]; (iii) enzyme; and (iv) distilled water added for a final volume of 6.0 mL. Enzymatic assays were conducted at a temperature of 37° C. The fatty acids formed during the hydrolytic enzymatic reaction were extracted with an organic solvent and titrated following the procedure described in U.S. Pat. No. 4,283,494.

A quantity of the lipase of the invention was used to determine its molecular weight. The molecular weight of the lipase of *P. alcaligenes* was found to be about 30,000 using sodium dodecyl sulfate polyacrylamide gel electrophoresis (SDS-PAGE) and comparing the relative mobility of the lipase with molecular weight calibration standards.

Part (C)- Production of the Lipase *P. alcaligenes* SD2 Using the Method of the Present Invention Cultures were grown in a sterile culture medium having the following composition:

| Culture Medium | |
| --- | --- |
| Ingredient | Weight Percent |
| $(NH_4)_2SO_4$ | 0.500 |
| $K_2HPO_4$ | 0.050 |
| $MgSO_4.7H_2O$ | 0.025 |
| $CaCl_2.2H_2O$ | 0.015 |
| TX114 | 0.536 |
| Tryptone | 2.000 |

The above listed ingredients were dissolved in deionized water. The final pH was neutral without adjustment. At temperatures above 18°-20° C., the medium will be cloudy due to phase separation by the Triton X-114. The medium was pressure-steam sterilized at 121° C.

An inoculum culture of *Pseudomonas alcaligenes* SD2 described in U.S. patent application Ser. No. 07/324,062 of 50 ml volume was grown in the medium described for 7-8 hours at 30° C. with shaking at 150-250 rpm and then transferred in toto to 950 ml of the same sterile medium. The larger culture is incubated 16 hours at 30° C. with shaking at 150-250 rpm in a 4 to 6 liter Erlenmeyer flask. This culture was then added aseptically in toto to 21 liters of sterile culture medium in a 30 L fermenter and incubated 24 hours at 30° C. with internal impeller agitation at 200-250 rpm and aeration at about 5 liters air per minute at a vessel atmospheric pressure of about 5 psig.

The culture was then chilled to below the cloud point (12°-15° C. was used in this example) and the cells removed by centrifugation using a refrigerated centrifuge operated at about 4° C. The clarified culture was then warmed above the cloud point (28° C. was used in this example) and recentrifuged using a centrifuge operated at about 28°-30° C. The Triton X-114 phase was thus separated and collected. In practice, the cell-free culture medium can be kept chilled until heated to about 28°-30° C. in the centrifuge, thus minimizing heating of the enzyme.

The Triton X-114 phase was then mixed with about an equal volume of 10 mM $CaCl_2.2H_2O$ below the cloud point. The solution was then warmed above the cloud point (30° C. was used) followed by centrifugation. This wash step was included to (1) increase the $Ca^{2+}$ level associated with the lipase, and (2) to remove any hydrophilic materials that may have contaminated the Triton X-114 phase.

The final yield of lipase was 281 LU/mL of Triton X-114 phase, or a total of 187,074 LU (LU refers to Lipase Unit, and is equivalent to 1 equivalent of fatty acid produced/minute at 37° C. from olive oil at pH 10.0). The recovery of lipase in this example was 63% of the amount produced in the culture. This compares favorably with a final yield of 155 LU/ml with a 20% recovery when using the comparison method described in Part (A) above, together with ammonium sulfate fractionation.

What is claimed is:

1. A process for providing simplified isolation of a lipase produced by *Pseudomonas alcaligenes* ATCC 53877 from a culture medium which comprises the steps of:
    (a) culturing said *Pseudomonas alcaligenes* ATCC 53877 in an aqueous culture medium comprising between about 0.5 and about 10 weight percent, based upon the volume of the culture medium, of polyoxyethylene p-t-octylphenol having a cloud point of less than 40° C. for a time sufficient to provide secretion of said lipase from said *Pseudomonas alcaligenes* ATCC 53877,
    (b) removing said *Pseudomonas alcaligenes* ATCC 53877 from said culture medium at a temperature below said cloud point to provide a microorganism-free solution,
    (c) heating said microorganism-free solution to a temperature above said cloud point to cause phase separation of said culture medium into an aqueous phase, and a non-aqueous phase containing said polyoxyethylene p-t-octylphenol and said lipase, and
    (d) isolating said non-aqueous phase containing said polyoxyethylene p-t-octylphenol and said lipase.

2. The process of claim 1 wherein steps (b) and (c) are carried out simultaneously.

3. The process of claim 1 wherein said polyoxyethylene p-t-octylphenol is employed in an amount such that the weight to volume concentration of said p-t-octylphenol is between about 0.5 and about 1% by weight based upon the volume of the culture medium.

* * * * *